United States Patent
Hoshino

(10) Patent No.: US 12,296,039 B2
(45) Date of Patent: May 13, 2025

(54) COMPOSITION WITH LONG-LASTING CONCEALING EFFECTS

(71) Applicant: L'OREAL, Paris (FR)

(72) Inventor: Akito Hoshino, Kanagawa (JP)

(73) Assignee: L'OREAL, Paris (FR)

(*) Notice: Subject to any disclaimer, the term of this patent is extended or adjusted under 35 U.S.C. 154(b) by 62 days.

(21) Appl. No.: 17/253,395

(22) PCT Filed: Jun. 12, 2019

(86) PCT No.: PCT/JP2019/024615
§ 371 (c)(1),
(2) Date: Dec. 17, 2020

(87) PCT Pub. No.: WO2020/004239
PCT Pub. Date: Jan. 2, 2020

(65) Prior Publication Data
US 2021/0251874 A1 Aug. 19, 2021

(30) Foreign Application Priority Data
Jun. 29, 2018 (JP) ................................ 2018-124349

(51) Int. Cl.
A61Q 1/10 (2006.01)
A61K 8/00 (2006.01)
A61K 8/19 (2006.01)
A61K 8/81 (2006.01)
A61Q 1/00 (2006.01)
A61Q 1/02 (2006.01)

(52) U.S. Cl.
CPC ............. A61K 8/8147 (2013.01); A61K 8/19 (2013.01); A61K 8/8117 (2013.01); A61Q 1/10 (2013.01); A61K 2800/5422 (2013.01); A61K 2800/5424 (2013.01); A61K 2800/59 (2013.01); A61K 2800/60 (2013.01); A61K 2800/805 (2013.01); A61K 2800/872 (2013.01)

(58) Field of Classification Search
CPC . A61Q 1/10; A61Q 19/00; A61Q 1/02; A61Q 1/00; A61Q 1/14; A61K 8/8152; A61K 2800/594; A61K 2800/43; A61K 2800/33; A61K 8/89; A61K 8/91; A61K 31/74; A61K 2800/548; A61K 2800/59
See application file for complete search history.

(56) References Cited

U.S. PATENT DOCUMENTS

| 2004/0096473 | A1* | 5/2004 | Jager-Lezer | A61K 8/027 424/401 |
| 2005/0163741 | A1 | 7/2005 | Zech | |
| 2013/0084256 | A1 | 4/2013 | Li et al. | |
| 2015/0079015 | A1* | 3/2015 | Bolognini | A61K 8/8152 424/70.7 |
| 2016/0136060 | A1* | 5/2016 | Crane | A61K 8/8152 424/63 |
| 2016/0136085 | A1* | 5/2016 | Crane | A61K 8/86 401/196 |
| 2017/0027844 | A1* | 2/2017 | Okura | A61K 8/19 |

FOREIGN PATENT DOCUMENTS

| DE | 102016124455 A1 | 6/2018 |
| JP | 2013-121949 A | 6/2013 |
| JP | 2014-024762 A | 2/2014 |
| JP | 5570140 B2 | 8/2014 |
| JP | 2015-124220 A | 7/2015 |
| JP | 5916438 B2 | 5/2016 |
| JP | 2017-210437 A | 11/2017 |
| WO | 2001/054660 A1 | 8/2001 |

(Continued)

OTHER PUBLICATIONS

Consumer Product Ingredients Database. Styrene/Acrylates/Ammonium Methacrylate Copolymer. Date Retrieved: Jan. 19, 2022. <https://www.productingredients.com/ingredient/info/styreneacrylatesammonium-methacrylate-copolymer>. (Year: 2022).*
OnlyTrainings.com. Emulsifiers in cosmetics; everything you need to know including selection factors. Date retrieved: Jan. 9, 2024. <https://onlytrainings.com/emulsifiers-in-cosmetics-everything-you-need-to-know-including-selection-factors-onlytrainings-blogs#>. (Year: 2024).*
PCT, International Search Report for the corresponding patent application No. PCT/JP2019/024615, dated Oct. 14, 2019.

(Continued)

Primary Examiner — Tracy Liu
(74) Attorney, Agent, or Firm — LUCAS & MERCANTI, LLP

(57) ABSTRACT

The present invention relates to a composition comprising: (a) at least one pigment; (b) at least one first copolymer of at least two monomers selected from (meth)acrylic acid, esters thereof, and salts thereof; (c) at least one second copolymer of styrene or α-methylstyrene and of at least one monomer selected from (meth)acrylic acid, esters thereof, and salts thereof, wherein the weight ratio of the amount of the (c) second copolymer(s)/the amount of the (a) pigment(s) is 1.0 or more, preferably 1.5 or more, and more preferably 2.0 or more, and the composition comprises at least one non-ionic surfactant in an amount of 0.5% by weight or less, preferably 0.3% by weight or less, and more preferably 0.1% by weight or less, relative to the total weight of the composition, or the composition comprises no non-ionic surfactant. The composition according to the present invention is suitable for a keratin substance such as the skin and the surface of a mucous membrane, and can provide the keratin substance with enhanced or improved cosmetic effects, such as better concealing effects of the original color of the keratin substance, as well as long-lasting makeup effects.

13 Claims, No Drawings

(56) References Cited

FOREIGN PATENT DOCUMENTS

| | | |
|---|---|---|
| WO | 2003/094868 A1 | 11/2003 |
| WO | 2008/145258 A1 | 12/2008 |
| WO | 2018/043971 A1 | 3/2018 |

OTHER PUBLICATIONS

JPO, Office Action for the corresponding Japanese patent application No. 2018-124349, dated Aug. 1, 2022, with English translation.
Notice of Allowance for the corresponding Japanese patent application No. 2018-124349, dated Jun. 26, 2023, with English translation.

\* cited by examiner

COMPOSITION WITH LONG-LASTING CONCEALING EFFECTS

CROSS REFERENCE TO RELATED APPLICATION

This Application is a 371 of PCT/JP2019/024615 filed on Jun. 12, 2019 which, in turn, claimed the priority of Japanese Patent Application No. 2018-124349 filed on Jun. 29, 2018, both applications are incorporated herein by reference.

TECHNICAL FIELD

The present invention relates to a composition suitable for a keratin substance, preferably a cosmetic composition, more preferably a makeup cosmetic composition, and in particular an eyeliner, as well as a process which relates to the composition.

BACKGROUND ART

There have been cosmetic compositions directed to a makeup for a keratin substance such as the skin and the surface of a mucous membrane, especially eye makeup products, for instance eyeliners, in particular in the form of pencils.

In general, these cosmetic compositions are required to conceal, for example, original skin color for makeup purposes, and it is preferable that this concealing can last a long time.

JP-B-5570140 and JP-B-5916438 disclose liquid cosmetic compositions for eyeliners and eyebrow pencils which include carbon black as well as a non-ionic surfactant or an acrylate copolymer as a film-forming agent.

DISCLOSURE OF INVENTION

There remains a need for an improved composition which possesses enhanced cosmetic effects for a keratin substance, such as concealing better original color of the keratin substance, and long-lasting property of this concealing effect even when in contact with sebum, fingers and the like during the use thereof.

An objective of the present invention is to provide a composition suitable for a keratin substance such as the skin and the surface of a mucous membrane, which can provide the keratin substance with enhanced or improved cosmetic effects, such as better concealing effect of the original color of the keratin substance, as well as long-lasting makeup effects.

The above objective can be achieved by a composition, comprising:
(a) at least one pigment;
(b) at least one first copolymer of at least two monomers selected from (meth)acrylic acid, esters thereof, and salts thereof;
(c) at least one second copolymer of styrene or a-methylstyrene and of at least one monomer selected from (meth)acrylic acid, esters thereof, and salts thereof, wherein
the weight ratio of the amount of the (c) second copolymer(s)/the amount of the (a) pigment(s) is 1.0 or more, preferably 1.5 or more, and more preferably 2.0 or more, and the composition comprises at least one non-ionic surfactant in an amount of 0.5% by weight or less, preferably 0.3% by weight or less, and more preferably 0.1% by weight or less, relative to the total weight of the composition, or the composition comprises no non-ionic surfactant.

The (a) pigment may be carbon black.

The amount of the (a) pigment in the composition may be 1% to 30% by weight, preferably 3% to 20% by weight, and more preferably 5% to 10% by weight, relative to the total weight of the composition.

The (meth)acrylic acid esters for the (b) first copolymer may be selected from alkyl(meth)acrylates with a $C_1$-$C_{30}$ alkyl radical, aryl(meth)acrylates with a $C_6$-$C_{10}$ aryl radical, and hydroxyalkyl(meth)acrylates with a $C_2$-$C_6$ hydroxyalkyl radical.

The amount of the (b) first copolymer in the composition may be 0.001% to 30% by weight, preferably 0.01% to 20% by weight, and more preferably 0.1% to 10% by weight, relative to the total weight of the composition.

The (c) second copolymer may have at least one ammonium moiety or group.

The (meth)acrylic acid esters for the (c) second copolymer may be selected from alkyl(meth)acrylates with a $C_1$-$C_{30}$ alkyl radical, aryl(meth)acrylates with a $C_6$-$C_{10}$ aryl radical, and hydroxyalkyl(meth)acrylates with a $C_2$-$C_6$ hydroxyalkyl radical.

The amount of the (c) second copolymer in the composition may be 1% to 40% by weight, preferably 5% to 35% by weight, and more preferably 10% to 30% by weight, relative to the total weight of the composition.

The (b) first copolymer and/or the (c) second copolymer may be in the form of particles.

The composition according to the present invention may comprise at least one anionic surfactant in an amount of 0.5% by weight or less, preferably 0.3% by weight or less, and more preferably 0.1% by weight or less, relative to the total weight of the composition, or the composition comprises no anionic surfactant.

The composition according to the present invention may further comprise (d) water.

The amount of the (d) water in the composition may be 10% to 60% by weight, preferably 20% to 50% by weight, and more preferably 25% to 47% by weight, relative to the total weight of the composition.

The composition according to the present invention may be a cosmetic composition, preferably a makeup composition, and more preferably an eyeliner composition.

Another aspect of the present invention relates to a cosmetic process for making up a keratin substance, comprising the step of applying onto the keratin substance the composition according to the present invention.

The present invention also relates to a process for preparing a composition, comprising the step of
mixing
(a) at least one pigment;
(b) at least one first copolymer of at least two monomers selected from (meth)acrylic acid, esters thereof, and salts thereof;
(c) at least one second copolymer of styrene or a-methylstyrene and of at least one monomer selected from (meth)acrylic acid, esters thereof, and salts thereof; and
(d) water,
wherein
the weight ratio of the amount of the (c) second copolymer(s)/the amount of the (a) pigment(s) in the composition is 1.0 or more, preferably 1.5 or more, and more preferably 2.0 or more; and
the (a) pigment(s) and the (b) first copolymer(s) are firstly mixed with (d) water to prepare an aqueous dispersion of the (a) pigment dispersed with the (b) first polymer, and then the mixture is further mixed with the (c) second copolymer(s).

BEST MODE FOR CARRYING OUT THE INVENTION

After diligent research, the inventors have discovered that it is possible to provide a composition suitable for a keratin substance such as the skin and the surface of a mucous membrane, which can provide the keratin substance with enhanced or improved cosmetic effects, such as better concealing effects of the original color of the keratin substance, as well as long lasting makeup effects.

Thus, the composition according to the present invention is a composition, comprising:
(a) at least one pigment;
(b) at least one first copolymer of at least two monomers selected from (meth)acrylic acid, esters thereof, and salts thereof;
(c) at least one second copolymer of styrene or a-methylstyrene and of at least one monomer selected from (meth)acrylic acid, esters thereof, and salts thereof,
wherein
the weight ratio of the amount of the (c) second copolymer(s)/the amount of the (a) pigment(s) is 1.0 or more, preferably 1.5 or more, and more preferably 2.0 or more, and the composition comprises at least one non-ionic surfactant in an amount of 0.5% by weight or less, preferably 0.3% by weight or less, and more preferably 0.1% by weight or less, relative to the total weight of the composition, or the composition comprises no non-ionic surfactant.

The composition according to the present invention can provide a keratin substance such as the skin and the surface of a mucous membrane with enhanced or improved cosmetic effects or properties, such as better color concealing effects and long-lasting makeup effects.

Hereafter, the composition, as well as the process, according to the present invention will be described in a detailed manner.

[Composition]
(Pigment)

The composition according to the present invention comprises (a) at least one pigment. If two or more pigments are used, they may be the same or different.

The pigments, which may be used according to the present invention, may be chosen from white or colored, inorganic or organic, polymeric or non-polymeric, and coated or uncoated pigments.

Representative examples of inorganic pigments include carbon black, titanium dioxide, zirconium oxide, zinc oxide, cerium oxide, iron oxide, chromium oxide, manganese violet, ultramarine blue, chromium hydrate, and ferric blue. The inorganic pigments may optionally be surface-treated. Carbon black is preferable.

Representative examples of organic pigments include carbon black, pigments of D&C type, and lakes based on cochineal carmine, barium, strontium, calcium, and aluminum.

The pigments may be pearlescent pigments or nacres.

The nacres which may be used according to the present invention may be chosen from white nacreous pigments such as mica coated with titanium or with bismuth oxychloride, colored nacreous pigments such as titanium mica with iron oxides, titanium mica with iron oxides, titanium mica with ferric blue or chromium oxide, titanium mica with an organic pigment chosen from those mentioned above, and nacreous pigments based on bismuth oxychloride.

The amount of the (a) pigment(s) in the composition according to the present invention may be 1% by weight or more, preferably 3% by weight or more, and more preferably 5% by weight or more, relative to the total weight of the composition. It may be even more preferable that the amount of the (a) pigment(s) in the composition according to the present invention be 6% by weight or more, relative to the total weight of the composition.

On the other hand, the amount of the (a) pigment(s) in the composition according to the present invention may be 30% by weight or less, preferably 20% by weight or less, and more preferably 10% by weight or less, relative to the total weight of the composition. It may be even more preferable that the amount of the (a) pigment(s) in the composition according to the present invention be 8% by weight or less, relative to the total weight of the composition.

Accordingly, the amount of the (a) pigment(s) in the composition may range from 1% to 30% by weight, preferably from 3% to 20% by weight, and more preferably from 5% to 10% by weight, relative to the total weight of the composition. It may be even more preferable that the amount of the (a) pigment(s) in the composition according to the present invention be from 6% to 8% by weight, relative to the total weight of the composition.

It is preferable to use the (a) pigment(s) in the form of an aqueous dispersion further comprising a polymer dispersant, preferably the (b) first copolymer as described below.

It is preferable that the aqueous dispersion of the (a) pigment(s) comprises a surfactant in an amount of 0.5% by weight or less, preferably 0.3% by weight or less, and more preferably 0.1% by weight or less, relative to the total weight of the aqueous dispersion, or the aqueous dispersion comprises no surfactant. By using the aqueous dispersion of the (a) pigment(s) comprising a surfactant in an amount of 0.5% by weight or less or no surfactant, a composition with better long-lasting makeup effects can be provided.

The aqueous dispersion comprises a polymer dispersant, preferably the (b) first copolymer in an amount 0.1% by weight or more, preferably 1% by weight or more, and more preferably 3% by weight or more, relative to the total weight of the aqueous dispersion. The aqueous dispersion comprises a polymer dispersant, preferably the (b) first copolymer in an amount 20% by weight or less, preferably 10% by weight or less, and more preferably 6% by weight or less, relative to the total weight of the aqueous dispersion.

It is preferable to use the aqueous dispersion of the (a) pigment(s) dispersed not by a surfactant but by a polymer dispersant for providing a cosmetic composition, in particular an eyeliner, with better long-lasting makeup effects.

(First Copolymer)

The composition according to the present invention comprises (b) at least one first copolymer. If two or more first copolymers are used, they may be the same or different.

The (b) first copolymer is a copolymer of at least two monomers selected from (meth)acrylic acid, esters thereof and salts thereof.

The (b) first copolymer can be prepared by copolymerization of at least two monomers selected from (meth)acrylic acid, esters thereof and salts thereof.

Styrene or α-methylstyrene is not used as the monomers for the (b) first copolymer. Thus, the (b) first copolymer is free from a unit derived from styrene or α-methylstyrene.

It is preferable that the (meth)acrylic acid esters for the (b) first copolymer be selected from alkyl(meth)acrylates with a $C_1$-$C_{30}$ alkyl radical, aryl(meth)acrylates with a $C_6$-$C_{10}$ aryl radical, and hydroxyalkyl(meth)acrylates with a $C_2$-$C_6$ hydroxyalkyl radical.

Among the alkyl(meth)acrylates, mention may be made of methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl(meth)acrylates, mention may be made of hydroxyethyl acrylate, 2-hydroxypropyl acrylate, hydroxyethyl methacrylate and 2-hydroxypropyl methacrylate.

Among the aryl(meth)acrylates, mention may be made of benzyl acrylate and phenyl acrylate.

The (meth)acrylic acid esters that are particularly preferred are the alkyl(meth)acrylates.

According to the present invention, the alkyl group of the esters may be either fluorinated or perfluorinated, i.e. some or all of the hydrogen atoms of the alkyl group are substituted with fluorine atoms.

The (meth)acrylic acid salts for the (b) first copolymer may be selected from metal salts or ammonium salts of (meth)acrylic acid. The metal salts may be alkaline metal salts such as sodium or potassium salts, or alkaline earth metal salts such as magnesium salts or calcium salts. The (meth)acrylic acid salts for the (b) first copolymer may be selected from ammonium salts of (meth)acrylic acid.

The (b) first copolymer may have at least one ammonium moiety or group. The ammonium moiety or group may be present as an ammonium salt moiety or group as a pendant group, or may be present in the main chain of a chemical structure such as the alkyl group of the alkyl(meth)acrylates.

The (b) first copolymer may be a copolymer of at least one monomer selected from (meth)acrylic acid ammonium salts, and of at least one monomer selected from esters of (meth) acrylic acid.

The (b) first copolymer may be ammonium acrylates copolymer such as Syntran PC5400 and Syntran KL219C sold by Interpolymer.

It may be preferable that the (b) first copolymer be a copolymer of at least one monomer selected from esters of (meth)acrylic acid with no ammonium moiety or group, and of at least one monomer selected from esters of (meth) acrylic acid with no ammonium moiety or group.

It may be preferable that the (b) first copolymer be acrylates copolymer such as Daitosol 3000SLPN-PE1 and Daitosol 3000VP3 sold by Daito.

It may be preferable that the composition of the present invention comprises two or more different acrylates copolymers. By combining two or more different acrylates copolymers, the pigment such as carbon black can be more stably dispersed in the composition according to the present invention. For example, Daitosol 3000SLPN-PE1 and Daitosol 3000VP3 above may be combined in the ratio from 10:1 to 1:1, preferably from 3:1 to 1.5:1.

The (b) first copolymer(s) may preferably be combined with, in particular, the (a) pigment(s) For example, the (b) first copolymer(s) may be used as dispersant(s) of the (a) pigment(s).

The (b) first copolymer(s) may be in the form of a particle or particles. The particles may have the volume average particle size of 100 nm or less.

The amount of the (b) first copolymer(s) in the composition according to the present invention may be 0.001% by weight or more, preferably 0.01% by weight or more, and more preferably 0.1% by weight or more, relative to the total weight of the composition. It may be even more preferable that the amount of the (b) first copolymer(s) in the composition according to the present invention be 1% by weight or more, relative to the total weight of the composition.

On the other hand, the amount of the (b) first copolymer(s) in the composition according to the present invention may be 30% by weight or less, preferably 20% by weight or less, and more preferably 10% by weight or less, relative to the total weight of the composition. It may be even more preferable that the amount of the (b) first copolymer(s) in the composition according to the present invention be 6% by weight or less, relative to the total weight of the composition.

Accordingly, the amount of the (b) first copolymer(s) in the composition may range from 0.001% to 30% by weight, preferably from 0.01% to 20% by weight, and more preferably from 0.1% to 10% by weight, relative to the total weight of the composition. It may be even more preferable that the amount of the (b) first copolymer(s) in the composition according to the present invention be from 1% to 6% by weight, relative to the total weight of the composition.

(Second Copolymer)

The composition according to the present invention comprises (c) at least one second copolymer. If two or more second copolymers are used, they may be the same or different.

The second copolymer is a copolymer of styrene or α-methylstyrene and of at least one monomer selected from (meth)acrylic acid, esters thereof, and salts thereof.

The (c) second copolymer can be prepared by copolymerization of styrene or α-methylstyrene and of at least one monomer selected from (meth)acrylic acid, esters thereof.

It is preferable that the (meth)acrylic acid esters for the (c) second copolymer be selected from alkyl(meth)acrylates with a $C_1$-$C_{30}$ alkyl radical, aryl(meth)acrylates with a $C_6$-$C_{10}$ aryl radical, and hydroxyalkyl(meth)acrylates with a $C_2$-$C_6$ hydroxyalkyl radical.

Among the alkyl(meth)acrylates, mention may be made of methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl(meth)acrylates, mention may be made of hydroxyethyl acrylate, 2-hydroxypropyl acrylate, hydroxyethyl methacrylate and 2-hydroxypropyl methacrylate.

Among the aryl(meth)acrylates, mention may be made of benzyl acrylate and phenyl acrylate.

The (meth)acrylic acid esters that are particularly preferred are the alkyl(meth)acrylates.

According to the present invention, the alkyl group of the esters may be either fluorinated or perfluorinated, i.e. some or all of the hydrogen atoms of the alkyl group are substituted with fluorine atoms.

It is preferable that the (meth)acrylic acid salts for the (c) second copolymer be selected from metal salts or ammonium salts of (meth)acrylic acid. The metal salts may be alkaline metal salts such as sodium or potassium salts, or alkaline earth metal salts such as magnesium salts or calcium salts. It is more preferable that the (meth)acrylic acid salts for the (b) first copolymer be selected from ammonium salts of (meth)acrylic acid.

It is preferable that the (c) second copolymer have at least one ammonium moiety or group. The ammonium moiety or group may be present as an ammonium salt moiety or group as a pendant group, or may be present in the main chain of a chemical structure such as the alkyl group of the alkyl (meth)acrylates.

It may be preferable that the (c) second copolymer be a copolymer of styrene, of at least one monomer selected from (meth)acrylic acid ammonium salts, and of at least one monomer selected from esters of (meth)acrylic acid.

It is may also be preferable that the (c) second copolymer be a copolymer of styrene, of at least one monomer selected from esters of (meth)acrylic acid with at least one ammonium moiety or group, and of at least one monomer selected from esters of (meth)acrylic acid with no ammonium moiety or group.

It may be more preferable that the (c) second copolymer be styrene/acrylates/ammonium methacrylate copolymer such as Syntran CG5760, Syntran 5009, and Syntran PC5620 sold by Interpolymer.

It is acceptable that the (c) second copolymer(s) not be used in combination with the (a) pigment(s). For example, it is acceptable that the (c) second copolymer(s) not be used as dispersant(s) of the (a) pigment(s). On the other hand, the (c) second copolymer(s) may be used as a film-forming agent.

The (c) second copolymer(s) may be in the form of a particle or particles.

The amount of the (c) second copolymer(s) in the composition according to the present invention may be 1% by weight or more, preferably 5% by weight or more, and more preferably 10% by weight or more, relative to the total weight of the composition. It may be even more preferable that the amount of the (c) second copolymer(s) in the composition according to the present invention be 14% by weight or more, relative to the total weight of the composition.

On the other hand, the amount of the (c) second copolymer(s) in the composition according to the present invention may be 40% by weight or less, preferably 35% by weight or less, and more preferably 30% by weight or less, relative to the total weight of the composition. It may be even more preferable that the amount of the (c) second copolymer(s) in the composition according to the present invention be 25% by weight or less, relative to the total weight of the composition.

Accordingly, the amount of the (c) second copolymer(s) in the composition may range from 1% to 40% by weight, preferably from 5% to 35% by weight, and more preferably from 10% to 30% by weight, relative to the total weight of the composition. It may be even more preferable that the amount of the (a) pigment(s) in the composition according to the present invention be from 14% to 25% by weight, relative to the total weight of the composition.

In the present invention, the weight ratio of the amount of the (c) second copolymer(s)/the amount of the (a) pigment(s) is 1.0 or more, preferably 1.5 or more, and more preferably 2.0 or more. It may be even more preferable that weight ratio of the amount of the (c) second copolymer(s)/ the amount of the (a) pigment(s) be 2.5 or more.

(Non-Ionic Surfactant)

The composition according to the present invention may comprise at least one non-ionic surfactant. If two or more non-ionic surfactants are used, they may be the same or different.

However, the amount of the non-ionic surfactant in the composition according to the present invention is limited such that the amount of the non-ionic surfactant is 0.5% by weight or less, preferably 0.3% by weight or less, and more preferably 0.1% by weight or less, relative to the total weight of the composition, or the composition comprises no non-ionic surfactant.

It is most preferable that the composition according to the present invention include no non-ionic surfactant.

The non-ionic surfactants are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$)alkylamine oxides or N—($C_{10}$-$C_{14}$) acylaminopropylmorpholine oxides; silicone surfactants; and mixtures thereof.

The non-ionic surfactants may preferably be chosen from monooxyalkylenated, polyoxyalkylenated, monoglycerolated or polyglycerolated non-ionic surfactants. The oxyalkylene units are more particularly oxyethylene or oxypropylene units, or a combination thereof, and are preferably oxyethylene units.

Examples of monooxyalkylenated or polyoxyalkylenated non-ionic surfactants that may be mentioned include:
  monooxyalkylenated or polyoxyalkylenated ($C_8$-$C_{24}$) alkylphenols,
  saturated or unsaturated, linear or branched, monooxyalkylenated or polyoxyalkylenated $C_8$-$C_{30}$ alcohols,
  saturated or unsaturated, linear or branched, monooxyalkylenated or polyoxyalkylenated $C_8$-$C_{30}$ amides,
  esters of saturated or unsaturated, linear or branched, $C_8$-$C_{30}$ acids and of polyalkylene glycols, monooxyalkylenated or polyoxyalkylenated esters of saturated or unsaturated, linear or branched, $C_8$-$C_{30}$ acids and of sorbitol,
  saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. Advantageously, the non-ionic surfactants do not comprise any oxypropylene units.

According to one of the embodiments of the present invention, the polyoxyalkylenated non-ionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated fatty alcohol (or $C_8$-$C_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 30 oxyethylene units (Ceteareth-10 to Ceteareth-30, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 10 to 30 oxyethylene units (Steareth-10 to Steareth-30, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

As examples of monoglycerolated or polyglycerolated non-ionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

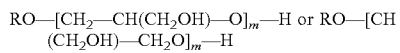

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The monoglycerolated or polyglycerolated $C_8$-$C_{40}$ fatty esters may correspond to the following formula:

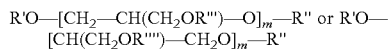

in which each of R', R" and R'" independently represents a hydrogen atom, or a linear or branched $C_8$-$C_{40}$ and preferably $C_8$-$C_{30}$ alkyl-CO— or alkenyl-CO-radical, with the proviso that at least one of R', R" and R'" is not a hydrogen atom, and m represents a number ranging from 1 to 30 and preferably from 1.5 to 10.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

According to one of the embodiments according to the present invention, the non-ionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name:

Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The non-ionic surfactant according to the present invention preferably contains alkenyl or branched $C_{12}$-$C_{22}$ acyl chain such as oleyl or isostearyl group. More preferably, the non-ionic surfactant according to the present invention is PEG-20 glyceryl triisostearate.

According to one of the embodiments according to the present invention, the non-ionic surfactant may be selected from copolymers of ethylene oxide and of propylene oxide, in particular copolymers of the following formula:

in which a, b and c are integers such that a+c ranges from 2 to 100 and b ranges from 14 to 60, and mixtures thereof.

According to one of the embodiments according to the present invention, the non-ionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

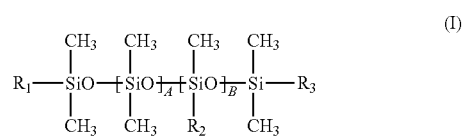

in which:
$R_1$, $R_2$ and $R_3$, independently of each other, represent a $C_1$-$C_6$ alkyl radical or a radical —$(CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being a hydrogen, an alkyl radical or an acyl radical;
A is an integer ranging from 0 to 200;
B is an integer ranging from 0 to 50; with the proviso that A and B are not simultaneously equal to zero;
x is an integer ranging from 1 to 6;
y is an integer ranging from 1 to 30;
z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

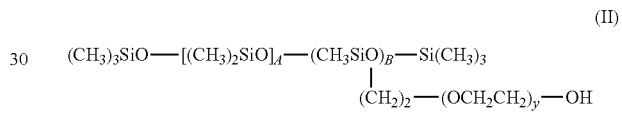

in which A is an integer ranging from 20 to 105, B is an integer ranging from 2 to 10 and y is an integer ranging from 10 to 20.

As examples of silicone surfactants of formula (I), mention may also be made of the compounds of formula (III):

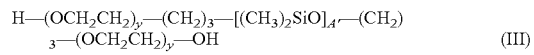

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; and A is 27, B is 3 and y is 12.

The compound Q4-3667 is a compound of formula (III) in which A is 15 and y is 13.

(Anionic Surfactant)

The composition according to the present invention may comprise at least one anionic surfactant. If two or more anionic surfactants are used, they may be the same or different.

It may be preferable that the amount of the anionic surfactant in the composition according to the present invention be limited such that the amount of the anionic surfactant is 0.5% by weight or less, preferably 0.3% by weight or less, and more preferably 0.1% by weight or less, relative to the total weight of the composition, or the composition comprises no anionic surfactant.

The anionic surfactants may be chosen in particular from anionic derivatives of proteins of vegetable origin or of silk proteins, phosphates and alkyl phosphates, carboxylates, sulphosuccinates, amino acid derivatives, alkyl sulphates, alkyl ether sulphates, sulphonates, isethionates, taurates, alkyl sulphoacetates, polypeptides, anionic derivatives of alkyl polyglucosides, and their mixtures.

1) Anionic derivatives of proteins of vegetable origin are protein hydrolysates comprising a hydrophobic group, it being possible for the said hydrophobic group to be naturally present in the protein or to be added by reaction of the protein and/or of the protein hydrolysate with a hydrophobic compound. The proteins are of vegetable origin or derived from silk, and the hydrophobic group can in particular be a fatty chain, for example an alkyl chain comprising from 10 to 22 carbon atoms. Mention may more particularly be made, as anionic derivatives of proteins of vegetable origin, of apple, wheat, soybean or oat protein hydrolysates comprising an alkyl chain having from 10 to 22 carbon atoms, and their salts. The alkyl chain can in particular be a lauryl chain and the salt can be a sodium, potassium and/or ammonium salt.

Thus, mention may be made, as protein hydrolysates comprising a hydrophobic group, for example, of salts of protein hydrolysates where the protein is a silk protein modified by lauric acid, such as the product sold under the name Kawa Silk by Kawaken; salts of protein hydrolysates where the protein is a wheat protein modified by lauric acid, such as the potassium salt sold under the name Aminofoam W OR by Croda (CTFA name: potassium lauroyl wheat amino acids) and the sodium salt sold under the name Proteol LW 30 by Seppic (CTFA name: sodium lauroyl wheat amino acids); salts of protein hydrolysates where the protein is an oat protein comprising an alkyl chain having from 10 to 22 carbon atoms and more especially salts of protein hydrolysates where the protein is an oat protein modified by lauric acid, such as the sodium salt sold under the name Proteol OAT (30% aqueous solution) by Seppic (CTFA name: sodium lauroyl oat amino acids); or salts of apple protein hydrolysates comprising an alkyl chain having from 10 to 22 carbon atoms, such as the sodium salt sold under the name Proteol APL (30% aqueous/glycol solution) by Seppic (CTFA name: sodium cocoyl apple amino acids). Mention may also be made of the mixture of lauroyl amino acids (aspartic acid, glutamic acid, glycine, alanine) neutralized with sodium N-methylglycinate sold under the name Proteol SAV 50 S by Seppic (CTFA name: sodium cocoyl amino acids).

2) Mention may be made, as phosphates and alkyl phosphates, for example, of monoalkyl phosphates and dialkyl phosphates, such as lauryl monophosphate, sold under the name MAP 20® by Kao Chemicals, the potassium salt of dodecyl phosphate, the mixture of mono- and diesters (predominantly diester) sold under the name Crafol AP-31® by Cognis, the mixture of octyl phosphate monoester and diester, sold under the name Crafol AP-20® by Cognis, the mixture of ethoxylated (7 mol of EO) 2-butyloctyl phosphate monoester and diester, sold under the name Isofol 12 7 EO-Phosphate Ester® by Condea, the potassium or triethanolamine salt of mono($C_{12}$-$C_{13}$)alkyl phosphate, sold under the references Arlatone MAP 230K-40® and Arlatone MAP 230T-60® by Uniqema, potassium lauryl phosphate, sold under the name Dermalcare MAP XC-99/09® by Rhodia Chimie, and potassium cetyl phosphate, sold under the name Arlatone MAP 160K by Uniqema.

3) Mention may be made, as carboxylates, of:
amido ether carboxylates (AEC), such as sodium lauryl amido ether carboxylate (3 EO), sold under the name Akypo Foam 30® by Kao Chemicals;
polyoxyethylenated carboxylic acid salts, such as oxyethylenated (6 EO) sodium lauryl ether carboxylate (65/25/10 $C_{12}$-$C_{14}$-$C_{16}$), sold under the name Akypo Soft 45 NV® by Kao Chemicals, polyoxyethylenated and carboxymethylated fatty acids originating from olive oil, sold under the name Olivem 400® by Biologia E Tecnologia, or oxyethylenated (6 EO) sodium tridecyl ether carboxylate, sold under the name Nikkol ECTD-6NEX® by Nikkol; and
salts of fatty acids (soaps) having a $C_6$ to $C_{22}$ alkyl chain which are neutralized with an organic or inorganic base, such as potassium hydroxide, sodium hydroxide, triethanolamine, N-methylglucamine, lysine and arginine.

4) Mention may in particular be made, as amino acid derivatives, of alkali salts of amino acids, such as:
sarcosinates, such as sodium lauroyl sarcosinate, sold under the name Sarkosyl NL 97® by Ciba or sold under the name Oramix L 30® by Seppic, sodium myristoyl sarcosinate, sold under the name Nikkol Sarcosinate MN® by Nikkol, or sodium palmitoyl sarcosinate, sold under the name Nikkol Sarcosinate PN® by Nikkol;
alaninates, such as sodium N-lauroyl-N-methylamidopropionate, sold under the name Sodium Nikkol Alaninate LN 30® by Nikkol or sold under the name Alanone ALE® by Kawaken, or triethanolamine N-lauroyl-N-methylalanine, sold under the name Alanone ALTA® by Kawaken;
glutamates, such as triethanolamine monococoyl glutamate, sold under the name Acylglutamate CT-12® by Ajinomoto, triethanolamine lauroyl glutamate, sold under the name Acylglutamate LT-12® by Ajinomoto;
aspartates, such as the mixture of triethanolamine N-lauroyl aspartate and triethanolamine N-myristoyl aspartate, sold under the name Asparack® by Mitsubishi;
glycine derivatives (glycinates), such as sodium N-cocoyl glycinate, sold under the names Amilite GCS-12® and Amilite GCK 12 by Ajinomoto;
citrates, such as the citric monoester of oxyethylenated (9 mol) coco alcohols, sold under the name Witconol EC 1129 by Goldschmidt; and
galacturonates, such as sodium dodecyl D-galactoside uronate, sold by Soliance.

5) Mention may be made, as sulphosuccinates, for example, of oxyethylenated (3 EO) lauryl (70/30 $C_{12}$/$C_{14}$) alcohol monosulphosuccinate, sold under the names Setacin 103 Special® and Rewopol SB-FA 30 K 4® by Witco, the disodium salt of a hemisulphosuccinate of $C_{12}$-$C_{14}$ alcohols, sold under the name Setacin F Special Paste® by Zschimmer Schwarz, oxyethylenated (2 EO) disodium oleamidosulphosuccinate, sold under the name Standapol SH 135® by Cognis, oxyethylenated (5 EO) lauramide monosulphosuccinate, sold under the name Lebon A-5000® by Sanyo, the disodium salt of oxyethylenated (10 EO) lauryl citrate monosulphosuccinate, sold under the name Rewopol SB CS 50® by Witco, or ricinoleic monoethanolamide monosulphosuccinate, sold under the name Rewoderm S 1333® by Witco. Use may also be made of polydimethylsiloxane sulphosuccinates, such as disodium PEG-12 dimethicone sulphosuccinate, sold under the name Mackanate-DC 30 by MacIntyre.

6) Mention may be made, as alkyl sulphates, for example, of triethanolamine lauryl sulphate (CTFA name: TEA lauryl sulphate), such as the product sold by Huntsman under the name Empicol TL40 FL or the product sold by Cognis under the name Texapon T42, which products are at 40% in aqueous solution. Mention may also be made of ammonium lauryl sulphate (CTFA name: ammonium lauryl sulphate), such as the product sold by Huntsman under the name Empicol AL 30FL, which is at 30% in aqueous solution.

7) Mention may be made, as alkyl ether sulphates, for example, of sodium lauryl ether sulphate (CTFA name: sodium laureth sulphate), such as that sold under the names Texapon N40 and Texapon AOS 225 UP by Cognis, or ammonium lauryl ether sulphate (CTFA name: ammonium laureth sulphate), such as that sold under the name Standapol EA-2 by Cognis.

8) Mention may be made, as sulphonates, for example, of α-olefinsulphonates, such as sodium α-olefinsulphonate ($C_{14}$-$C_{16}$), sold under the name Bio-Terge AS-40® by Stepan, sold under the names Witconate AOS Protégé® and Sulframine AOS PH 12® by Witco or sold under the name Bio-Terge AS-40 CG® by Stepan, secondary sodium olefinsulphonate, sold under the name Hostapur SAS 30® by Clariant; or linear alkylarylsulphonates, such as sodium xylenesulphonate, sold under the names Manrosol SXS30®, Manrosol SXS40® and Manrosol SXS93® by Manro.

9) Mention may be made, as isethionates, of acylisethionates, such as sodium cocoylisethionate, such as the product sold under the name Jordapon CI P® by Jordan.

10) Mention may be made, as taurates, of the sodium salt of palm kernel oil methyltaurate, sold under the name Hostapon CT Paté® by Clariant; N-acyl-N-methyltaurates, such as sodium N-cocoyl-N-methyltaurate, sold under the name Hostapon LT-SF® by Clariant or sold under the name Nikkol CMT-30-T® by Nikkol, Sodium Methyl Stearoyl Taurate sold under the name Nikkol SMT® or sodium palmitoyl methyltaurate, sold under the name Nikkol PMT® by Nikkol.

11) The anionic derivatives of alkyl polyglucosides can in particular be citrates, tartrates, sulphosuccinates, carbonates and glycerol ethers obtained from alkyl polyglucosides. Mention may be made, for example, of the sodium salt of cocoylpolyglucoside (1,4) tartaric ester, sold under the name Eucarol AGE-ET® by Cesalpinia, the disodium salt of cocoylpolyglucoside (1,4) sulphosuccinic ester, sold under the name Essai 512 MP® by Seppic, or the sodium salt of cocoylpolyglucoside (1,4) citric ester, sold under the name Eucarol AGE-EC® by Cesalpinia.

For the amino acid derivatives, it is preferable that they be chosen from acyl glycine derivatives or glycine derivatives, in particular acyl glycine salt.

The acyl glycine derivatives or glycine derivatives can be chosen from acyl glycine salts (or acyl glycinates) or glycine salts (or glycinates), and in particular from the following.

i) Acyl glycinates of formula (I):

R—HNCH$_2$COOX     (I)

in which
R represents an acyl group R'C=O, with R', which represents a saturated or unsaturated, linear or branched, hydrocarbon chain, preferably comprising from 10 to 30 carbon atoms, more preferably from 12 to 22 carbon atoms, even more preferably from 14 to 22 carbon atoms and better still from 16 to 20 carbon atoms, and X represents a cation chosen, for example, from the ions of alkali metals, such as Na, Li or K, preferably Na or K, the ions of alkaline earth metals, such as Mg, ammonium groups and their mixtures.

The acyl group can in particular be chosen from the lauroyl, myristoyl, behenoyl, palmitoyl, stearoyl, isteaaroyl, olivoyl, cocoyl or oleoyl groups and their mixtures.

Preferably, R is a cocoyl group.

ii) Glycinates of the following formula (II):

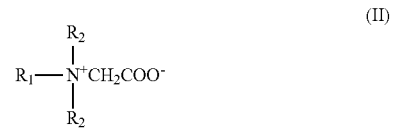

in which:

$R_1$ represents a saturated or unsaturated, linear or branched, hydrocarbon chain comprising from 10 to 30 carbon atoms, preferably from 12 to 22 carbon atoms and better still from 16 to 20 carbon atoms; $R_1$ is advantageously chosen from the lauryl, myristyl, palmityl, stearyl, cetyl, cetearyl or oleyl groups and their mixtures and preferably from the stearyl and oleyl groups, the $R_2$ groups, which are identical or different, represent an R"OH group, R" being an alkyl group comprising from 2 to 10 carbon atoms, preferably from 2 to 5 carbon atoms.

Mention may be made, as the compound of formula (I), for example, of the compounds carrying the INCI name sodium cocoyl glycinate, such as, for example, Amilite GCS-12, sold by Ajinomoto, or potassium cocoyl glycinate, such as, for example, Amilite GCK-12 from Ajinomoto.

Use may be made, as compounds of formula (II), of dihydroxyethyl oleyl glycinate or dihydroxyethyl stearyl glycinate.

Preferably the anionic surfactants are not soaps. Thus, preferably the anionic surfactants are chosen from synthetic anionic surfactants. More preferably, the anionic surfactants are chosen from amido ether carboxylates; alkyl sulfates; alkyl ether sulfates; olefin sulfonates and acylisethionates; and mixtures thereof.

It is preferable that the (a) anionic surfactant be selected from the group consisting of:

sodium laureth sulfate, ammonium laureth sulfate, disodium lauryl sulfosuccinate, disodium laureth sulfosuccinate, diammonium lauryl sulfosuccinate, diethylhexyl sodium sulfosuccinate, sodium oleyl succinate, sodium lauroyl methyl isethionate, sodium lauryl isethionate, sodium cocoyl isethionate, sodium laureth-5 carboxylate, lauryl ether carboxylic acid, ammonium lauryl sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, potassium lauryl sulfate, potassium laureth sulfate, ammonium cocoyl sulfate, ammonium lauroyl sulfate, sodium cocoyl sulfate, sodium lauroyl sulfate, potassium cocoyl sulfate, monoethanolamine cocoyl sulfate, sodium tridecyl benzene sulfonate, sodium dodecyl benzene sulfonate, sodium C14-16 olefin sulfonate, sodium lauryl sarcosinate, sodium lauroyl sarcosinate, stearoyl sarcosine, lauryl sarcosine, cocoyl sarcosine, sodium methyl cocoyl taurate, sodium methyl lauroyl taurate, sodium lauroyl glutamate, disodium cocoyl glutamate, potassium myristoyl glutamate, TEA-cocoyl glutamate, sodium cocoyl glycinate, potassium cocoyl glycinate, sodium cocoyl alaniate, TEA-cocoyl alaninate and mixtures thereof.

[Water]

The composition according to the present invention may comprise (d) water, preferably deionized water.

The amount of the (d) water in the composition according to the present invention may be from 10 to 60% by weight, preferably from 20 to 50% by weight, more preferably from 25 to 47% by weight, and even more preferably from 30 to 40% by weight, relative to the total weight of the composition.

(Other Optional Additives)

The composition according to the present invention may also comprise any other optional additive(s) usually used in the field of cosmetics, chosen, for example, from oils, cationic or amphoteric surfactants in an amount of 0.5% by weight or less, preferably 0.3% by weight or less, and more preferably 0.1% by weight or less, relative to the total weight of the composition, solvents, gums, resins, hydrophilic thickening agents such as hydroxypropylcellulose, hydrophobic thickening agents such as dimethicone crosspolymers, dispersants other than the above ingredient (b), antioxidants, film-forming agents other than the above ingredient (c), preserving agents such as phenoxyethanol, fragrances, neutralizers, antiseptics, UV-screening agents, cosmetic active agents, such as vitamins, moisturizers, emollients or collagen-protecting agents, and mixtures thereof.

The composition according to the present invention can also comprise at least one alkaline agent, such as triethanolamine, tromethamine, aminomethyl propanediol, and aminomethyl propanol. The amount of the alkaline agent in the composition according to the present invention may be from 0.05% to 1% by weight, preferably from 0.1% to 0.5% by weight, relative to the total weight of the composition. By adding an alkaline agent, the pigment such as carbon black can be more stably dispersed in the composition according to the present invention.

The composition according to the present invention can also comprise at least one water-miscible solvent such as a lower monoalcohol containing from 1 to 5 carbon atoms, $C_3$-$C_4$ ketones or $C_3$-$C_4$ aldehydes. The water-miscible solvent that can preferably be used is ethanol. The content of water-miscible solvent can range from 0.1% to 15% by weight, and better still from 1% to 8% by weight, relative to the total weight of the composition.

It is a matter of routine operations for a person skilled in the art to adjust the nature and amount of the above optional additives which may be present in the composition in accordance with the present invention such that the desired cosmetic properties are not thereby affected.

[Preparation]

The composition according to the present invention can be prepared by mixing the above-described essential and optional ingredients in a conventional manner.

For example, the composition according to the present invention can be prepared by a process comprising the step of mixing (a) at least one pigment;

(b) at least one first copolymer of at least two monomers selected from (meth)acrylic acid, esters thereof, and salts thereof;

(c) at least one second copolymer of styrene or α-methylstyrene and of at least one monomer selected from (meth)acrylic acid, esters thereof, and salts thereof, such that the weight ratio of the amount of the (c) second copolymer(s)/the amount of the (a) pigment(s) in the composition is 1.0 or more, preferably 1.5 or more, and more preferably 2.0 or more, and the composition may comprise at least one non-ionic surfactant in an amount of 0.5% by weight or less, preferably 0.3% by weight or less, and more preferably 0.1% by weight or less, relative to the total weight of the composition, or the composition may comprise no non-ionic surfactant.

It is possible to further mix any of the optional ingredients.

It may be preferable that (d) water is also mixed with the ingredients (a), (b) and (c).

It may be more preferable that the (a) pigment(s) and the (b) first copolymer be mixed firstly, preferably with (d) water, to prepare a mixture of the (a) pigment and the (b) first polymer(s), preferably an aqueous dispersion of the (a) pigment dispersed with the (b) first polymer, and then the mixture be further mixed with the (c) second copolymer(s) to obtain the composition according to the present invention.

The mixing can be performed at any temperature such as room temperature (e.g., 25° C.), preferably at a temperature of 30° C. or more, preferably 40° C. or more, and more preferably 50° C. or more. It is preferable to further mix with any of the above-described optional ingredients.

It is preferable that the cosmetic composition according to the present invention be in the form of a liquid, preferably a dispersion of the (a) pigment(s), and more preferably an aqueous dispersion of the (a) pigment(s).

[Cosmetic Use and Process]

The composition according to the present invention may be a cosmetic composition, preferably a makeup cosmetic composition (in particular, an eye makeup cosmetic composition), and more preferably an eyeliner.

The cosmetic composition according to the present invention can be used for cosmetic treatments, preferably makeup, of a keratin substance such as the skin and the surface of a mucous membrane such as edges of eyelids.

For example, the composition according to the present invention can be used for a cosmetic process for making up a keratin substance such as the skin and the surface of a mucous membrane comprising the step of applying onto the keratin substance the composition according to the present invention.

The composition according to the present invention can provide cosmetic, in particular makeup, effects such as concealing of the original color of the keratin substance. Furthermore, the composition according to the present invention can exert long-lasting makeup effects.

EXAMPLES

The present invention will be described in a more detailed manner by way of examples. However, these examples should not be construed as limiting the scope of the present invention. The examples below are presented as non-limiting illustrations in the field of the invention.

Example 1 to 2 and Comparative Examples 1 to 4

[Preparations]

The following compositions according to Examples (Ex.) 1 to 2 and Comparative Examples (Comp. Ex.) 1 to 4, shown in Table 1, were prepared by mixing the components shown in Table 1 at room temperature (25° C.). The numerical values for the amounts of the components shown in Table 1 are all based on "% by weight" as active raw materials unless otherwise indicated.

TABLE 1

| | Ex. 1 | Ex. 2 | Comp. Ex. 1 | Comp. Ex. 2 | Comp. Ex. 3 | Comp. Ex. 4 |
|---|---|---|---|---|---|---|
| Butylene Glycol | 6 | 6 | 6 | 6 | 6 | 6 |
| Phenoxyethanol | 0.5 | 0.5 | 0.5 | 0.5 | 0.5 | 0.5 |
| Caprylyl Glycol | 0.5 | 0.5 | 0.5 | 0.5 | 0.5 | 0.5 |
| Water | 35.07 | 46.07 | 32.67 | 35.07 | 42.27 | 33.07 |
| Disodium EDTA | 0.03 | 0.03 | 0.03 | 0.03 | 0.03 | 0.03 |
| Triehtanolamine | 0.3 | 0.3 | 0.3 | 0.3 | 0.3 | 0.3 |
| Black 2/Acrylates Copolymer/Butylenen Glycol/Phenoxyethanol *1 | 21.6 (5.4) | 21.6 (5.4) | — | — | 21.6 (5.4) | 21.6 (5.4) |
| Black 2/Butylene Glycol/Ammonium Acrylates Copolymer/Phenoxyethanol (PE-Black 15AD, MIKUNI COLOR) *2 | — | — | 50 (7.5) | — | — | — |
| Black 2/Laureth-21/PEG-40 Hydrogenated Castor Oil/Sodium Dehydroacetate (WD-CB2, DAITO KASEI KOGYO) *3 | — | — | — | 21.6 (5.4) | — | — |
| PPG-2 Butyl Ether | — | — | — | — | — | 2.0 |
| Styrene/Acrylates/Ammonium Methacrylate Copolymer/Sodium Laureth Sulfate (and) Caprylyl Glycol (SYNTRAN 5760 CG, INTERPOLYMER) *4 | 36 (14.4) | 25 (10.0) | 10 (4.0) | 36 (14.4) | — | 36 (14.4) |
| Acrylates Copolymer emulsion (Daitosol 5000AD, DAITO KASEI KOGYO) *5 | — | — | — | — | 28.8 (14.4) | — |
| Total | 100.00 | 100.00 | 100.00 | 100.00 | 100.00 | 100.00 |
| Styrene/Acrylates/Ammonium Methacrylate Copolymer/Carbon Black | 2.66 | 1.85 | 0.53 | 2.66 | — | 2.66 |
| Long Lasting Effect | Very Good | Fair | Poor | Poor | Poor | Poor |
| Blackness | Very Good | Good | Good | Fair | Fair | Good |

*1 Content rate of carbon black: 25 wt % (the amount of carbon black is shown in parentheses in Table 1), Content rate of Acrylates Copolymer: 7.5 wt %, Carbon black is dispersed in water with Acrylates Copolymer as a polymer dispersant
*2 Content rate of carbon black: 15 wt % (the amount of carbon black is shown in parentheses in Table 1), Content rate of Ammonium Acrylates Copolymer: 15 wt %, Carbon black is dispersed in water with Ammonium Acrylates Copolymer as a polymer dispersant
*3 Content rate of carbon black: 25 wt % (the amount of carbon black is shown in parentheses in Table 1), Carbon black is dispersed in water with Laureth-21 and PEG-40 Hydrogenated Castor Oil as a surfactant
*4 Content rate of styrene/acrylates/ammonium methacrylate copolymer: 40 wt % (the amount of styrene/acrylates/ammonium methacrylate copolymer is shown in parentheses in Table 1)
*5 Solid content rate: 50 wt% (the amount of acrylates copolymer is shown in parentheses in Table 1)

[Evaluations]
(Long Lasting Effect)

Each of the compositions according to Examples 1 and 2, and Comparative Examples 1-4 was filled in a liquid pen type package as an eyeliner, and a line was drawn on the back of the hand of a panelist. After drying for 10 minutes, artificial sebum with the formulation shown in Table 2 was dripped on the line, followed by rubbing it with a finger 30 times. The aspects of the line were evaluated by visual observation.

Very Good: No flakes or smudges were observed
Good: Almost no flakes or smudges were observed
Fair: Small flakes or smudges were observed
Poor: Line was not maintained

TABLE 2

| Artificial Sebum Formulation | |
|---|---|
| | wt % |
| Triisostearin | 28.7 |
| Hydrogenated Polyisobutene | 13.7 |
| Oleic Acid | 28.0 |
| Oleyl Erucate | 22.9 |
| Octyl Dodecanol | 6.7 |
| Total | 100 |

The results are shown in Table 1.
(Blackness)

Each of the compositions according to Examples 1 and 2, and Comparative Examples 1~4 was filled in a liquid pen type package as an eyeliner, and 5 lines were drawn on the back of the hand of a panelist. The blackness of the lines was evaluated by visual observation.

Very Good: Skin color was completely concealed by the black lines
Good: Skin color was concealed by the black lines
Fair: Most of the skin color was concealed by the black lines
Poor: Skin color was not concealed by the black lines The results are shown in Table 1.

(Summary)

The composition according to Example 1, which includes the acrylates copolymer as the (b) first copolymer and styrene/acrylates/ammonium methacrylate copolymer as the (c) second copolymer wherein the weight ratio of the amount of the (c) second copolymer/the amount of the carbon black is 2.0 or more, shows the best results in terms of both long-lasting effect and blackness.

The composition according to Example 2, which includes the (b) first copolymer and the (c) styrene/acrylates/ammonium methacrylate copolymer wherein the weight ratio of the amount of the (c) second copolymer/the amount of the carbon black is 1.5 or more, shows cosmetically acceptable results in terms of both long-lasting effect and blackness.

The composition according to Comparative Example 1, which includes the (b) first copolymer and the (c) styrene/acrylates/ammonium methacrylate copolymer wherein the weight ratio of the amount of the (c) second copolymer/the amount of the carbon black is less than 1.0, did not show long-lasting cosmetic effects.

The composition according to Comparative Example 2, which includes carbon black dispersed with non-ionic surfactants (laureth-21 and PEG-40 hydrogenated castor oil) instead of acrylates copolymer, did not show long-lasting cosmetic effects.

The composition according to Comparative Example 3, which includes acrylates copolymer instead of styrene/acrylates/ammonium methacrylate copolymer, did not show long-lasting cosmetic effects.

The composition according to Comparative Example 4, which includes a substantial amount of a non-ionic surfactant (PPG-2 butyl ether) in addition to the composition according to Example 1, did not show long-lasting cosmetic effects.

The invention claimed is:

1. A composition, comprising:
    (a) carbon black, in an amount of 1% to 30% by weight, relative to the total weight of the composition;
    (b) at least one first copolymer selected from the group consisting of acrylates copolymer, ammonium acrylates copolymer, and a mixture thereof, in an amount of 0.001% to 30% by weight, relative to the total weight of the composition; and
    (c) a second copolymer being styrene/acrylates/ammonium methacrylate copolymer, in an amount of 1% to 40% by weight, relative to the total weight of the composition,
    wherein
    the composition is in a form of a liquid,
    the weight ratio of the amount of the (c) second copolymer/the amount of the (a) carbon black is in a range of 2.0 to 3.0, and
    the composition comprises no non-ionic surfactant.

2. The composition according to claim 1, wherein the amount of the (a) carbon black in the composition is 3% to 20% by weight relative to the total weight of the composition.

3. The composition according to claim 1, wherein the amount of the (b) at least one first copolymer in the composition is 0.01% to 20% by weight relative to the total weight of the composition.

4. The composition according to claim 1, wherein the amount of the (c) second copolymer in the composition is 5% to 35% by weight relative to the total weight of the composition.

5. The composition according to claim 1, wherein the (b) at least one first copolymer and/or the (c) second copolymer is/are in the form of particles.

6. The composition according to claim 1, wherein the composition comprises at least one anionic surfactant in an amount of 0.5% by weight or less relative to the total weight of the composition, or the composition comprises no anionic surfactant.

7. The composition according to claim 1, wherein the composition further comprises (d) water.

8. The composition according to claim 7, wherein the amount of the (d) water in the composition is 10% to 60% by weight relative to the total weight of the composition.

9. The composition according to claim 1, wherein the composition is an eyeliner.

10. The composition according to claim 1, wherein the composition is an aqueous dispersion comprising no surfactant.

11. A cosmetic process for making up a keratin substance, comprising the step of:
    applying onto the keratin substance the composition according to claim 1.

12. The cosmetic process according to claim 11, wherein the keratin substance is a skin or a mucous membrane.

13. A process for preparing a composition, comprising the step of mixing
    (a) carbon black, in an amount of 1% to 30% by weight, relative to the total weight of the composition;
    (b) at least one first copolymer selected from the group consisting of acrylates copolymer, ammonium acrylates copolymer, and a mixture thereof, in an amount of 0.001% to 30% by weight, relative to the total weight of the composition;
    (c) a second copolymer being styrene/acrylates/ammonium methacrylate copolymer, in an amount of 1% to 40% by weight, relative to the total weight of the composition;
    and
    (d) water,
    wherein
    the composition is in a form of a liquid;
    the composition comprises no non-ionic surfactant;
    the weight ratio of the amount of the (c) second copolymer/the amount of the (a) carbon black in the composition is in a range of 2.0 to 3.0; and
    the (a) carbon black and the (b) first copolymer(s) are firstly mixed with (d) water to prepare an aqueous dispersion of the (a) carbon black dispersed with the (b) first copolymer(s), and then the mixture is further mixed with the (c) second copolymer.

* * * * *